United States Patent [19]

Gibson et al.

[11] Patent Number: 5,240,843
[45] Date of Patent: Aug. 31, 1993

[54] ENZYME STABILISATION

[75] Inventors: Timothy D. Gibson, Leeds, England; John R. Woodward, Xenia, Ohio

[73] Assignee: Cranfield Biotechnology Ltd., Cranfield Beds, United Kingdom

[21] Appl. No.: 721,424

[22] PCT Filed: Nov. 13, 1989

[86] PCT No.: PCT/GB89/01346

§ 371 Date: Jun. 27, 1991

§ 102(e) Date: Jun. 27, 1991

[87] PCT Pub. No.: WO90/05182

PCT Pub. Date: May 17, 1990

[30] Foreign Application Priority Data

Nov. 11, 1988 [GB] United Kingdom ............... 8826429

[51] Int. Cl.$^5$ ........................ C12N 9/02; C12N 9/98
[52] U.S. Cl. ............................ 435/188; 435/25; 435/189
[58] Field of Search .................... 435/188, 189, 25

[56] References Cited

U.S. PATENT DOCUMENTS

| | | | |
|---|---|---|---|
| 3,133,001 | 5/1964 | Muset | 435/188 |
| 3,413,198 | 11/1968 | Deutsch | 435/188 |
| 3,950,133 | 4/1976 | Monte et al. | 435/188 |
| 3,950,223 | 4/1976 | Yugari et al. | 435/188 |
| 4,011,169 | 3/1977 | Diehl et al. | 435/188 |
| 4,465,770 | 8/1984 | Modrovich | 435/188 |
| 4,824,938 | 4/1989 | Koyama et al. | 435/188 |
| 4,950,596 | 8/1990 | Cheng et al. | 435/188 |
| 4,965,203 | 10/1990 | Silbering et al. | 435/188 |
| 5,102,788 | 4/1992 | Cole | 435/188 |

FOREIGN PATENT DOCUMENTS

| | | |
|---|---|---|
| 0074237 | 3/1983 | European Pat. Off. . |
| 0166427 | 1/1986 | European Pat. Off. . |
| 2182997 | 12/1973 | France . |
| 0107178 | 6/1983 | Japan ................. 435/188 |
| 0111686 | 7/1983 | Japan ................. 435/188 |
| 1139384 | 6/1986 | Japan ................. 435/188 |
| 2036189 | 2/1987 | Japan ................. 435/188 |
| 1253137 | 11/1971 | United Kingdom ......... 435/188 |
| 2090599A | 7/1982 | United Kingdom . |

OTHER PUBLICATIONS

Wang et al. "Technical Report No. 10" Parenteral Formulations of Proteins & Peptide: Stability & Stabilizers vol. 42 Suppl 1988 S4–S26.

Back et al. "Biochem" vol. 18 No. 23 1979 pp. 5191–5197.

Chemical Abstracts, vol. 106, 1987, Abstract No. 115739X.

Primary Examiner—Herbert J. Lilling
Attorney, Agent, or Firm—Darby & Darby

[57] ABSTRACT

A method of stabilising enzymes or other proteins against denaturation or drying comprises mixing the protein with a cyclic polyol and a cationic polyelectrolyte.

27 Claims, No Drawings

ENZYME STABILISATION

This invention relates to stabilisation of proteins, particularly but not exclusively of enzymes in the dry state.

Few enzymes are inherently stable in solution. Many have a tendency to become denatured when held in solution. Various workers have attempted to stabilise enzymes either by adding compounds such as sugars or glycerol to solutions of them or by freeze drying. These methods often cause a loss of activity. Alternative methods of stabilisation have involved drying of enzymes with stabilisers in a presence of a solid support such as cellulose fibre or polyacrylamide. U.S. Pat. No. 4,451,569 disclosed stabilisation of glutathione peroxidase by freezing the enzyme with one of a number of sugars including arabinose, glucose, xylitol and sorbitol. Freeze drying is expensive to operate on a large scale and often results in denaturation.

PCT/GB86/00396 discloses stabilisation of proteins by use of the disaccharide trehalose.

According to a first aspect of the present invention a method of protecting proteins against denaturation on drying comprises mixing an aqueous solution of the protein with a soluble cationic polyelectrolyte and a cyclic polyol, and removing water from the solution.

Stabilisation in accordance with this invention enhances the activity of freshly dried enzymes and other proteins. The stability upon storage is also enhanced.

The proteins may include enzymes, antibodies, antigens, serum complement, vaccine components and bioactive peptides.

Drying of proteins and especially enzymes is important for many applications, for example use in diagnostic or analytical aids such as test strips which may be stored for prolonged periods before use. Transportation of enzymes or other proteins in solution is inconvenient and expensive.

Although freeze drying may be employed, The present invention facilitates use of the vacuum drying and air drying without denaturation. Vacuum drying and air drying milder processes and are much cheaper to operate.

The cyclic polyol may incorporate one or more alicyclic rings and may have at least one side chain. Compounds having 5 to 10 hydroxyl groups may be preferred. Non-reducing polyols are preferred. Di and trisaccharides are particularly efficaceous but other cyclic polyols, for example inositol may also be used. The polyol may be chosen to suit both the enzyme or other protein and also the polyelectrolyte in question. Lactitol, lactose, maltose and sucrose are especially preferred in conjunction with DEAE-dextrin, lactitol having been found to be most suitable for many applications. Sorbitol is suitable for use with cholesterol oxidase, cholesterol esterase and other enzymes. Cellobiose may also be used. The amount of polyol may lie in the preferred range of 1 to 20%, more preferably 2 to 10%, most preferably 5 to 10%.

The cationic polyelectrolyte is preferably a polymer with cationic groups distributed along the molecular chain. The cationic groups, which are preferably quaternary ammonium derived functions, may be disposed in side groups pendent from the chain or may be incorporated in it. Natural or artificial polymers may be employed. Natural polymers such as polysaccharides are preferred since many artificial polymers contain residual traces of the inorganic polymerisation catalyst.

Diethylaminoethyl dextran (DEAE-dextran) and chitosan are preferred although polyethyleneimine is also suitable. Polysaccharides with MW 5000 to 500 000, preferably 5000 to 20 000, more preferably 5000 to 10 000 may be employed. An amount of 0.1 to 10% is preferred, especially 0.5 to 2%.

The pH at which enzymes are dried in accordance with this invention may be important to optimise retention of activity both upon drying and after subsequent storage. The optimum pH for a particular enzyme may be determined by simple experimentation.

Alcohol oxidase has been formed to retain activity between pH 7 and 8, preferably at pH 7.8.

Cholesterol oxidase, dependent on the source, dries best at pH 5 or 9.

Uricase may be dried at pH 9.

Cholesterol esterase dependent on source may be dried at pH 7 or 9.

Drying is preferably performed in the presence of a wetting agent. Temperatures between 4° and 50°, especially 25° to 35° are preferred.

According to a second aspect of the present invention there is provided a dried product containing a protein, cyclic polyol and cationic polyelectrolyte.

The dried product may be a free running powder or may comprise part of a test strip or other analytical or diagnostic apparatus.

The present invention is now described by means of example but not in any limitative sense.

Experimental Procedures

Percentages used in the specification are by weight unless indicated otherwise.

All the stabilisation systems utilise buffers to maintain stable pH conditions e.g.

Buffer solutions containing $Na_2HPO_4 \cdot 2H_2O$ (10.855 g) and $NaH_2PO_4 \cdot 2H_2O$ (6.084 g) were dissolved in 1.0 liter distilled water to give a solution of pH 7.0 at a concentration of 100 millimoles per liter.

An alternative buffer is MOPS—(4-Morpholine Propane Sulphuric Acid) —52.25 g/2.5l distilled water pH to 7.87 with 4.0M.NaOH.

A wetting agent may be used dependent on whether or not the enzyme system is being stabilised in a polystyrene cuvette. A suitable wetting agent is protein hydrolysate from gelatine termed Byco A. These are made up to 1% w/v in phosphate buffer, 100 mmol. $l^{-1}$, pH 7.0 as needed.

Enzyme solutions were made up freshly before use. Stock solutions of enzymes in ammonium sulphate solution were dialysed exhaustively against buffer e.g. 100 mmol. $l^{-1}$ phosphate buffer pH 7.0 to remove all salts.

Stock enzyme concentrations may be from 10 to 1000 units of activity per milliliter of solution. In terms of protein concentration this is between 0.5 to 200 mgcm$^{-3}$. Typically the final protein concentration was 1.0 mgcm$^{-3}$.

Soluble polyelectrolyte, polyols, enzyme, buffer salts and wetting agent (if used) were mixed at constant temperature and dried in a vacuum oven over dessicant e.g. silica gel, 0.1 mm/Hg, 30° C. for 4–10 hr.

The oxidase enzymes studied may be assayed by colorimetric detection of the hydrogen peroxide produced by action of the enzyme. Peroxidase acts on the hydrogen peroxide produced in the presence of aromatic alcohols or amines and the heterocyclic compound 4-aminoantipyrine to give quinoneimine dyes. Other standard assays systems may be employed e.g. u.v. spectrometry.

The following systems were employed:

| System 1 | |
|---|---|
| Phenol sulphonic acid | 25 mmol.l$^{-1}$ |
| 4-aminoantipyrine | 0.4 mmol.l$^{-1}$ |
| Peroxidase | 1000 unit/l |
| The resultant dye was measured at 500 nm. | |
| System 2 | |
| 3,5-dichloro 2-hydroxybenzene sulphonic acid | 10 mmol.l$^{-1}$ |
| 4-aminoantipyrine | 0.4 mmol.l$^{-1}$ |
| Peroxidase | 1000 units/l |
| The resultant dye was measured at 520 nm. | |

Standard temperature e.g. 25° C. and incubation times e.g. 5 minutes were used. Reagent blanks contained all components except substrate. Dry preparations in cuvettes were reconstituted with Systems 1, or 2, directly.

Dry powered preparations were reconstituted with phosphate buffer and suitable aliquots were added to System 1, or 2.

For stability trials the storage temperature was 37° C., with samples being removed periodically to check for residual activity of the enzyme. This procedure was standard for all enzymes tested.

SOLUBLE POLYELECTROLYTE AND SUGAR ALCOHOL OR SACCHARIDE

Soluble Polyelectrolyte

Soluble polyelectrolyte was dissolved in distilled water a concentration up to 20% w/v, usually to 10% w/v. Sugar alcohol or saccharide was dissolved in distilled water up to a concentration of 40% w/v, usually to 20% w/v. These solutions were used within 4 weeks of preparation, being stored in the cold at 4° C.

EXAMPLE 1

| Solution 1 | DEAE-Dextran 10% | 100 ul |
|---|---|---|
| | Lactitol 20% | 500 ul |
| | Byco A 1% | 100 ul |
| Solution 2 | Alcohol oxidase 7 units (1.7 mg protein Phospbate buffer 100 mmol.l$^{-1}$ pH 7.0 | 35 ul 265 ul |

Solution 1 was stirred continuously whilst slowly adding Solution 2 at 4° C. The mixture was stirred for 5 minutes to ensure complete mixing. 0.1 ml volumes were dried in cuvettes as described, stored at 37° C. and assayed for activity as described

EXAMPLE 2

| Solution 1 | Alcohol oxidase 2 411 units (= 422 mg protein) in phosphate buffer | 2.7 cm$^3$ 300 mmol.l$^{-1}$ |
|---|---|---|
| Solution 2 | Lactitol 20% w/v DEAE-Dextran 10% w/v | 3.0 cm$^3$ 0.27 cm$^3$ |

Solution 2 was added slowly to Solution 1 with stirring. The mixed solutions were pipetted into petri dishes and vacuum dried over silica gel at 30° C. for 8 hours whereupon a thin glassy film of dried enzyme and stabiliser was produced. This was removed and ground to a fine powder using a glass pestle and mortar.

For stability testing 10 mg portions of enzyme powder were weighed into sterile polystyrene tubes and incubated at 37° in a sealed container over silica gel. Samples were removed periodically and reconstituted in distilled water. 60 ul of reconstituted enzyme solution was added to each assay cuvette containing peroxidase and colour reagents as described (Table 2).

EXAMPLE 3

| Solution 1 | DEAE-Dextran 10% w/v | 100 ul |
|---|---|---|
| | Lactitol 20% w/v | 500 ul |
| | Byco A 1% w/v | 100 ul |
| Solution 2 | Choline oxidase 10 units (0.794 mg protein) in phosphate pH 7.0 100 cm$^3$ | 300 ul |

Solution 2 was added with stirring to Solution 1 and thoroughly mixed at 4° C. 0.1 cm$^3$ volumes were vaccum dried in cuvettes as described, stored at 37° C. and assayed for activity as described (Table 3).

EXAMPLE 4

Glycerol 3 Phosphate Oxidase

| Solution 1 | DEAE-Dextran 10% w/v | 100 ul |
|---|---|---|
| | Lactitol 20% w/v | 500 ul |
| | Byco A 1% w/v | 100 ul |
| Solution 2 | Glycerol 3 Phosphate Oxidase 10 units (0.526 mg protein) in phosphate buffer pH 7.0 100 mmol.l$^{-1}$ | 300 ul |

Solution 2 was added with stirring to Solution 1 at 4° C. and thoroughly mixed. 0.1 cm$^3$ volume were vacuum dried in cuvettes as described (Table 4).

EXAMPLE 5

| Solution 1 | DEAE-Dextran 10% | 100 ul |
|---|---|---|
| | Lactose 20% | 500 ul |
| | Byco A 1% | 100 ul |
| Solution 2 | Alcohol oxidase 5 units (1.0 mg protein in 100 mmol.l$^{-1}$ Phosphate buffer pH 7.0 | 300 ul |

Solution 1 was stirred continuously whilst slowly adding Solution 2 at 4° C. The mixture being stirred for 5 minutes to ensure complete mixing 0.1 cm$^3$ volumes were dried in cuvettes as described (Table 5).

Soluble Polysaccharides

Soluble polysaccharides were dissolved in distilled water up to a concentration of 30% w/v usually to a concentration of 10% w/v. These solutions were used within 4 weeks of preparation and stored at 4° C.

EXAMPLE 6

| Solution 1 | Dextran (molecular wt. 10 000) 10% w/v | 100 ul |
|---|---|---|
| | Byco A 1% w/v | 100 ul |
| | Distilled water | 500 ul |
| Solution 2 | Alcohol oxidase 7 units (1.32 mg protein) in 100 mmol.l$^{-1}$ Phosphate buffer pH 7.0 | 300 ul |

Solution 2 was added to Solution 1 with stirring at 4° C. and stirring was continued for 5 minutes to ensure complete mixing. 0.1 cm³ volumes were vacuum dried in cuvettes, stored at 37° C. and assayed for activity as described.

When dextrans of differing molecular weights are used variations in stability were noted (Table 6).

EXAMPLE 7

| Solution 1 | Dextran molecular wt. 10 000 10% w/v solution | 500 ul |
| | Phosphate buffer 10 mmol.l⁻¹ pH 7.0 | 300 ul |
| Solution 2 | Galactose oxidase 0.52 units (0.8 mg protein) in 10 mmol.l⁻¹ phosphate buffer pH 7.0 | 200 ul |

Solution 2 was added to Solution 1 with stirring at 4° C. and stirring was continued for 5 minutes to ensure complete mixing. 0.1 ml aliquots were vacuum dried, stored at 37° C. and assayed for activity as described (Table 7).

Cyclic Polyalcohol

Cyclic polyalcohol was dissolved in distilled water to a concentration of 10% w/v. The solutions were stored at 4° C. and used within 4 weeks of preparation.

EXAMPLE 8

| Solution 1 | Inositol 10% w/v | 500 ul |
| | Distilled water | 200 ul |
| Solution 2 | Alcohol oxidase 4.7 units 91.15 mg/protein) in Phosphate buffer 100 mmol.l⁻¹ | 200 ul |

Solution 2 was added to Solution 1 with stirring at 4° C. and stirring was continued for 5 minutes to ensure complete mixing. 0.1 cm³ aliquots were vacuum dried, stored at 37° C. and assayed for activity as described (Table 8).

EXAMPLE 9

| Solution 1 | Inositol 10% w/v | 500 ul |
| | Phosphate buffer 100 mmol.l⁻¹ pH 7.0 | 300 ul |
| Solution 2 | Galactose oxidase 0.52 units (0.8 mg protein) in 10 mmol.l⁻¹ phosphate buffer pH 7.0 | 200 ul |

Solution 2 was added to Solution 1 with stirring at 4° C. and stirring was continued for 5 minutes to ensure complete mixing. 0.1 cm³ aliquots were vacuum dried as described, stored at 37° C. and assayed for activity as described (Table 9).

EXAMPLE 10

The following results show the stabilisation of alcohol oxidase (*Hansenula polymorpha*).

Unstabilised enzyme retained 26% activity after 7 days incubation at 37° C. Addition of chitosan above gave retention of 48.9% activity after 9 days. The activity in relation to freshly dried enzyme was measured after incubation at 37° C.

| Stabiliser | Period of incubation/days | Activity/% |
| --- | --- | --- |
| lactitol 5% | 1 | 86.9 |
| chitosan 0.1% | 6 | 85.7 |
| | 9 | 82.1 |
| | 16 | 86.1 |
| lactitol 5% | 1 | 87.4 |
| chitosan 0.01% | 6 | 87.2 |
| | 9 | 83.4 |
| | 16 | 91.6 |
| lactitol 5% | 1 | 79.3 |
| polyethyleneimine 0.1% | 6 | 77.5 |
| | 9 | 76.1 |
| | 16 | 77.5 |
| lactitol 5% | 1 | 91.1 |
| Polyethyleneimine 0.01% | 6 | 84.4 |
| | 9 | 96.1 |
| | 16 | 93.1 |
| lactitol 5% | 1 | 94.9 |
| DEAE-Dextran 0.1% | 6 | 85.1 |
| | 9 | 88.7 |
| | 16 | 90.6 |
| lactitol 5% | 1 | 98.3 |
| DEAE-Dextran 0.01% | 6 | 88.8 |
| | 9 | 89.4 |
| | 16 | 95.9 |

EXAMPLE 11

The following results show stabilisation of alcohol oxidase (*Pichia pastoris*). Unstabilised enzyme retained 49.8% and 36.1% activities after 2 days and 13 days respectively at 37° C. Enhanced activity (i.e. greater than 1-%) upon drying may be attributable to selective degradation of inhibiting impurities.

| Stabiliser | Period of incubation days | Activity/% |
| --- | --- | --- |
| lactitol 5% | 1 | 102.5 |
| DEAE-Dextran 1% | 4 | 116.6 |
| | 8 | 121.3 |
| | 15 | 104.3 |
| dextran 5% | 1 | 83.2 |
| | 4 | 97.0 |
| | 8 | 101.7 |
| | 15 | 87.6 |
| inositol 5% | 1 | 88.0 |
| | 4 | 106.2 |
| | 8 | 107.1 |
| | 15 | 109.1 |

EXAMPLE 12

The following results illustrate stabilisation of cholesterol oxidase (*Nocardia erythropolis*). Unstabilised enzyme retained 34.3% activity after 14 days at 37° C.

| Stabiliser | Period of incubation days | Activity/% |
| --- | --- | --- |
| lactitol 5% | 3 | 96.2 |
| DEAE-dextran 1% | 5 | 105.6 |
| | 14 | 115.7 |
| inositol 5% | 1 | 92.6 |
| | 7 | 84.8 |
| | 10 | 91.7 |

EXAMPLE 13

The following results illustrate stabilisation of freeze dried uricase.

| Stabiliser | Period of incubation days | Activity/% |
|---|---|---|
| lactitol 5% | 1 | 109.9 |
| DEAE-dextran 1% | 5 | 114.3 |
|  | 10 | 109.9 |

EXAMPLE 14

The following results illustrate stabilisation of various enzymes with lactitol (15%) and DEAE-dextran (1%) during drying in comparison to the activity of undried enzymes.

| Enzyme | Activity after drying/% Unstabilised | Stabilised |
|---|---|---|
| Alcohol oxidase (Pichia) | 64.7 | 78.2 |
| Choline oxidase | 63.3 | 97.7 |
| Lactate oxidase | 77.1 | 90.0 |
| Alcohol oxidase (Hensenula polymorpha) | 68.2 | 119.6 |
| Cholesterol oxidase |  |  |
| (vacuum dried) | 80.0 | 92.5 (inositol 5%) |
| (freeze dried) | 79.0 | 91.0 (inositol 5%) |

TABLE 1

| Preparation | Incubation 37° C. | % Activity remaining relative to activity freshly dried enzyme |
|---|---|---|
| Alcohol oxidase + Lactitol 10% DEAE-Dextran 1% | 1 day | 108 |
|  | 7 days | 120 |
|  | 14 days | 114 |
|  | 21 days | 106 |
|  | 5 months | 102 |

Unstabilised Enzyme retained 26% activity after 7 days

TABLE 2

| Bulk preparation | Incubation 37° C. | % Activity retained relative to freshly dried enzyme |
|---|---|---|
| DEAE-Dextran 1% Lactitol 10% Alcohol oxidase 7.25 units/10 mg solid | 4 days | 138 |
|  | 12 days | 121 |

Unstabilised Enzyme retained 34% activity after 4 days.

TABLE 3

| Bulk preparation | Incubation 37° C. | % Activity remaining relative to freshly dried enzyme |
|---|---|---|
| Choline oxidase DEAE-Dextran 1% Lactitol 10% | 1 day | 99 |
|  | 5 days | 84 |
|  | 10 days | 81 |
|  | 15 days | 83 |

Unstabilised Enzyme retained 24% of activity after 1 day, decreasing to 11% after 5 days.

TABLE 4

| Preparation | Incubation 37° C. | % Activity remaining relative to freshly dried enzyme |
|---|---|---|
| Glycerol 3 phosphate oxidase DEAE-Dextran 1% | 1 days | 104 |
|  | 5 days |  |
|  | 10 days | 117 |

TABLE 4-continued

| Preparation | Incubation 37° C. | % Activity remaining relative to freshly dried enzyme |
|---|---|---|
| Lactitol 10% | 15 days | 113 |

Unstabilised enzyme retained 94% activity after 1 day but only retained 54% activity after 15 days.

TABLE 5

| Preparation | Incubation 37° C. | % Activity remaining relative to freshly dried enzyme |
|---|---|---|
| Alcohol oxidase | 1 day | 137 |
| DEAE-Dextran 1% wt/vol | 6 days | 103 |
| Lactose 10% wt/vol | 10 days | 108 |
|  | 15 days | 92 |

Unstabilised enzyme retained 23% of activity after 10 days at 37° C.

TABLE 6

| Preparation | % Activity remaining (relative to freshly dried enzyme) | | | |
|---|---|---|---|---|
| Alcohol oxidase + Dextran 1% wt/vol | 1 day 37° C. | 6 days 37° C. | 18 days 37° C. | 11 months 37° C. |
| M Wt. |  |  |  |  |
| T10 10 000 | 93 | 87 | 73 | 77 |
| T40 40 000 | 82 | 75 | 61 | 64 |
| T70 70 000 | 84 | 86 | 65 | 60 |
| T500 500 000 | 83 | 86 | 62 | 49 |
| T2000 2 000 000 | 45 | 43 | 22 | 14 |

Unstabilised enzyme retained 30% of activity after 6 days.

TABLE 7

Galactose oxidase
Dextran concentrations 5% (M.W 10 000).

| Incubation 37° C. | % Activity remaining relative to activity of freshly dried enzyme. |
|---|---|
| 1 day | 92% |
| 7 days | 87% |
| 10 days | 82% |

TABLE 8

| Preparation | Incubation 37° C. | % Activity remaining relative to freshly dried enzyme |
|---|---|---|
| Alcohol oxidase + 5% Inositol | 1 Day | 150% |
|  | 7 days | 196% |
|  | 14 days | 166% |
|  | 23 days | 178% |

Unstabilised enzyme retained 26% activity after 7 days.

TABLE 9

| Preparation | Incubation 37° C. | % Activity remaining relative to freshly dried enzyme |
|---|---|---|
| Galactose oxidase + 5% Inositol | 1 day | 85% |
|  | 4 days | 78% |
|  | 10 days | 74% |

We claim:

1. A method for preparing a stabilised dried enzyme comprising the steps of:
   mixing an aqueous solution of an enzyme with a soluble polymeric cationic polyelectrolyte and a polyol comprising mono-, di-, trisaccharides, or reduced derivative thereof to form a mixture, and
   removing water from the mixture so as to obtain the stabilised dried enzyme.

2. A method as claimed in claim 1, wherein said polyelectrolyte comprises a quaternary ammonium functionalised polysaccharide.

3. A method as claimed in claim 2, wherein said polyelectrolyte comprises diethylaminoethyl-dextran or chitosan.

4. A method as claimed in claim 1, wherein the polyelectrolyte comprises polyethyleneimine.

5. A method as claimed in claim 1, wherein the polyol is a di or trisaccharide.

6. A method as claimed in claim 5 wherein the polyol comprises lactitol, lactose, maltose, sucrose or cellobiose.

7. A method as claimed in claim 1, wherein water is removed at a temperature ranging between 4° and 50° C.

8. A method as claimed in claim 7, wherein the temperature ranges between 25° and 35° C.

9. A method as claimed in claim 1, wherein the polyol comprises lactitol, sorbitol, inositol, lactose, maltose, sucrose, or cellobiose.

10. A method as claimed in claim 1, wherein the enzyme is present in the aqueous solution at a concentration ranging from 0.5 to 200 mg/mL.

11. A method as claimed in claim 10, wherein the enzyme is present in the aqueous solution at a concentration of 1 mg/mL.

12. A method as claimed in claim 1, wherein the enzyme is present in the aqueous solution at a concentration ranging from 0.5 to 1000 units/mL.

13. A method as claimed in claim 1, wherein the amount of the polyol ranges from 1 to 20%.

14. A method as claimed in claim 13, wherein the amount of the polyol ranges from 2 to 10%.

15. A method as claimed in claim 14, wherein the amount of said polyol ranges from 5 to 10%.

16. A method as claimed in claim 1, wherein the amount of said polyelectrolyte ranges from 0.1 to 10%.

17. A method as claimed in claim 16, wherein the amount of said polyelectrolyte ranges from 0.5 to 2%.

18. A dried product containing an oxidase, a soluble polymeric cation polyelectrolyte and a polyol comprising mono-, di-, trisaccharides, or reduced derivative thereof.

19. A dried product as claimed in claim 18 wherein said polyelectrolyte is a quaternary ammonium functionalised polymeric polysaccharide.

20. A dried product as claimed in claim 18, wherein said polyelectrolyte is polyethyleneimine.

21. A dried product as claimed in claim 18, wherein said polyol is a di or trisaccharide.

22. A dried products as claimed in claim 18, wherein the amount of said polyol ranges from 1 to 20%.

23. A dried product as claimed in claim 22, wherein the amount of said polyol ranges from 2 to 10%.

24. A dried product as claimed in claim 23, wherein the amount iof said polyol ranges from 5 to 10%.

25. A dried product as claimed in claim 18, wherein the amount of said polyelectrolyte ranges from 0.1 to 10%.

26. A dried product as claimed in claim 25, wherein the amount of said polyelectrolyte ranges from 0.5 to 10%.

27. A dried product as claimed in claim 18, wherein the polyol comprises lactitol, sorbitol, inositol, lactose, maltose, sucrose, or cellobiose.

* * * * *